(12) United States Patent
Schleimer et al.

(10) Patent No.: US 6,599,914 B2
(45) Date of Patent: Jul. 29, 2003

(54) INHIBITION OF CYTOKINE GENERATION

(75) Inventors: Robert P. Schleimer, Baltimore, MD (US); John Schroeder, Baltimore, MD (US); William Kreutner, West Paterson, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/841,506

(22) Filed: Apr. 24, 2001

(65) Prior Publication Data

US 2002/0183344 A1 Dec. 5, 2002

(51) Int. Cl.[7] .............................................. A61K 31/48
(52) U.S. Cl. ....................... 514/291; 514/292; 514/826; 514/849; 514/853; 514/854; 514/885; 514/886; 514/887
(58) Field of Search ................................ 514/290, 291, 514/292, 826, 849, 853, 854, 885, 886, 887

(56) References Cited

U.S. PATENT DOCUMENTS 5,595,997 A * 1/1997 Aberg et al. ................. 514/290

OTHER PUBLICATIONS

Dorland's Illustrated Medical Dictionary, 26th Edition, 1981, pp. 299, 368–369.
Lippert, U., et al, "Pharmacological modulation of IL–6 and IL–8 secretion . . . ", *Experimental Dermatology*, 1995, vol. 4, pp. 272–276.
Molet, S., et al, *Clinical and Experimental Allergy*, "Inhibitory activity of loratadine . . . " 1997, vol. 27, pp. 1167–1174.
Genovese, A., "Loratadine and desethoxylcarbonyl–loratadine . . . ", *Clinical and Experimental Allergy*, 1997, vol. 27, pp. 559–567.
Kleine–Tebbe, J., et al, "Inhibition of IgE–and non–IgE–mediated histamine. . .", *J. Allergy Clin. Immunol.*, 1994, vol. 23, No. 2, pp. 494–500.
Schroeder, John T., "The Role of Basophil–Cytokine Networks in Asthma", *Asthma and Allergic Disease*, 1998, pp. 75–86.
Lipozencic J., The EAACI 1997 Annual Meeting, *Acta Dermatovenerological Grotica*, 1997, pp. 69–80.
*Federal Register*, Oct. 5, 1998, vol. 63, No. 192, p. 53444.
Gibbs, B.F., "Inhibition of interleukin–4 and interleukin–13 . . . ", *Arch Pharmacol.*, 1998, pp. 573–578.
Kleine–Tebbe, J., "Influence of Descarbo, ethoxy–loratadine . . . ", *Clinic of Dermatology & OPD*, 1992, vol. 89, No. 1, Part 2, p. 277.
Segura, T., "Allergic Rhinitis: Basic Pathophysiology and Therapeutic Strategies", *Can. J. of Allergy & Clin. Immunol.*, 1999, vol. 4, No. 7, pp. 318–330.
Hayashi S., et al., "Anti–Inflammatory actions of new antihistamines", *Clinical and Experimental Allergy*, (1999) vol. 29 (12), pp. 1593–1596.

* cited by examiner

*Primary Examiner*—Frederick Krass
(74) *Attorney, Agent, or Firm*—Thomas D. Hoffman

(57) ABSTRACT

Methods of inhibiting the generation of pro-inflammatory cytokines such as IL-4 and IL-13 in a human patient in need of such inhibiting are disclosed.

4 Claims, 5 Drawing Sheets

INHIBITION OF CYTOKINE GENERATION

BACKGROUND OF THE INVENTION

The present invention relates to methods of using desloratadine to inhibit generation of pro-inflammatory cytokines, e.g., IL-4 and IL-13.

Mast cells and basophils play a role in allergic and inflammatory diseases. These cells produce a wide variety of mediators such as prostaglandins, e.g., prostaglandin D2, leukotrienes, e.g., leukotriene $C_4$ cytokines and histamine. Cytokines are polypeptides secreted by cells that affect the function of other cells. Cytokines, including interleukins, differ widely in the types of cells affected and in biological activities exhibited. Desloratadine, a non-sedating antihistamine, is disclosed by Lippert, U., et al, *Experimental Dermatology*, 1995, Vol. 4, 272–276 to be active in vitro in inhibiting the release of the cytokines IL-6 by up to 40% and IL-8 by up to 50% from human mast and basophilic cell lines. Human $Fc\epsilon$ $RI^+$ cells play a considerable pro-inflammatory role through the release of histamine, tryptase and chymase. However, since human mast and basophilic cell lines are defective in signaling through the high affinity immunoglogulin-E(IgE) receptor, $Fc\epsilon$ RI, it is difficult to predict what effect, if any, desloratadine has on the IgE-mediated release of IL-6 and IL-8. . S. Molet, et al., *Clinical and Experimental Allergy*, 1997, Vol. 27, pages 1167–1174 disclose that desloratadine reduces histamine-induced release of IL-6 and IL-8 in an in vitro study in endothelial cells. Kleine-Tebbe, J., et al, *J. Allergy Clin. Immunol.* 1994, Vol. 93, No. 2, pages 494–500 disclose that desloratadine inhibits IgE- and non-IgE-mediated histamine release in an in vitro study in human basophilic leukocyte cells.

Human basophils are a major source of the cytokines, IL-4 and IL-13 that are produced in vitro in mixed leukocyte cultures. Production of IL-4 and IL-13 by basophils may play a role in modulating a variety of activities that are involved in the pathogenesis of allergic inflammatory conditions. For example, IL-4 and IL-13 each induce secretion of IgE- and IgG-4 by human B-cells. (See Schroeder, J. T.,"The role of basophil-cytokine networks in asthma." In Asthma and Allergic Diseases: Physiology, Immunopharmacology, and Treatment, Editors: G. Marone, K. F. Austen, S T Holgate, A. B. Kay, L. M. Lichtenstein, Academic Press, San Diego, 75–84, 1998a). However, there is a no information on the effect of desloratadine on the generation of cytokines such as IL-4 and IL-13 in basophils or any other cell types. One study by Gibbs, et al. Naunyn Schmiedebegs Arch. Pharmacol, 1998, Vol. 357: 573–578 reports moderate (50%) inhibition of IL-4 and IL-13 secretion in vitro in basophilic cells using relatively high concentrations of terfenadine, a non-sedating antihistamine. This study did not test whether the terfenadine concentrations used were toxic. The FDA has withdrawn the two terfenadine NDAs because of the finding that terfenadine was no longer safe for cardiac reasons for use in treating seasonal allergic rhinitis.(Federal Register, Oct. 5,1998, Vol. 63, page 53444).

There is a need for a safe, effective therapy to inhibit secretion of pro-inflammatory cytokines such as IL-4 and IL-13 to treat disease states, for example, allergic and/or inflammatory conditions.

SUMMARY OF THE INVENTION

The present invention provides a method of inhibiting generation of IL-4 and IL-13 in a human patient in need of such inhibiting which comprises administering to such a patient an effective amount of desloratadine.

Typically. IL-4 and IL-13 is generated from human basophils as well as other cells, e.g., human B-cells.

The present invention also provides a method of inhibiting generation of IL-4 and IL-13 from human basophils in a patient exhibiting the symptoms of an allergic and/or inflammatory condition which comprises administering to such a patient an amount of desloratadine effective to inhibit the generation of IL-4 and IL-13 and to concurrently treat the symptoms of such an allergic and/or inflammatory conditions.

The present invention also provides a method of blocking generation of pro-inflammatory cytokines in a patient in need of such blocking which comprises administering to such a patient an effective amount of desloratadine.

The present invention also provides a method of inhibiting secretion of pro-inflammatory cytokines from human basophils in a patient in need of such inhibiting which comprises administering to such a patient an effective amount of desloratadine.

The preferred pro-inflammatory cytokines are IL-4 and IL-13.

The patients in need of such inhibiting are those having symptoms of allergic/inflammatory conditions of the airway passages, skin, eyes and intestinal tract.

The present invention also provides a method of treating a patient exhibiting the symptoms of allergic/inflammatory conditions of the skin, eyes, intestinal tract,and/or upper and lower airway passages which comprises administering to such a patient an effective amount of desloratadine.

The patients in need of such inhibiting are those having symptoms of an allergic and/or inflammatory condition of the skin, eyes, intestinal tract, and/or the upper and lower airway passages.

The present invention also provides a method of treating a disease state that has an allergic component and an inflammatory component which comprises administering to a patient in need of such treatment an amount of desloratadine effective to produce an anti-inflammatory effect.

The present invention also provides a method of treating and/or preventing allergic asthma and inhibiting secretion of IL-4 and IL-13 in a patient in need of such treating which comprises administering to such a patient an effective amount of desloratadine.

The present invention also provides a method of treating and/or preventing allergic rhinitis and inhibiting secretion of IL-4 and IL-13 in a patient in need of such treating which comprises administering to such a patient an effective amount of desloratadine.

The present invention also provides a method of treating and/or preventing atopic dermatitis and inhibiting secretion of IL-4 and IL-13 in a patient in need of such treating which comprises administering to such a patient an effective amount of desloratadine.

The present invention also provides a method of treating and/or preventing urticaria and inhibiting secretion of IL-4 and IL-13 in a patient in need of such treating which comprises administering to such a patient an effective amount of desloratadine.

The present invention also provides a method of treating IL-4 and IL-13 mediated disease states in a patient in need of such treating which comprises administering to such patients an effective amount of desloratadine to inhibit generation of IL-4 and IL-13.

The effective amount of desloratadine is an amount sufficient to inhibit and preferably block generation of IL-4 and IL-13 from human cells.

The present invention also provides a method of inhibiting generation of IL-4 and IL-13 from human basophils in a patient exhibiting the symptoms of an allergic and/or inflammatory condition of the skin, eyes, intestinal tract, and/or the upper and lower airway passages which comprises administering to such a patient an amount of desloratadine effective to inhibit the generation of IL-4 and IL-13 and to concurrently treat the symptoms of such an allergic and/or inflammatory condition.

DETAILED DESCRIPTION OF THE INVENTION

Figure 1A:
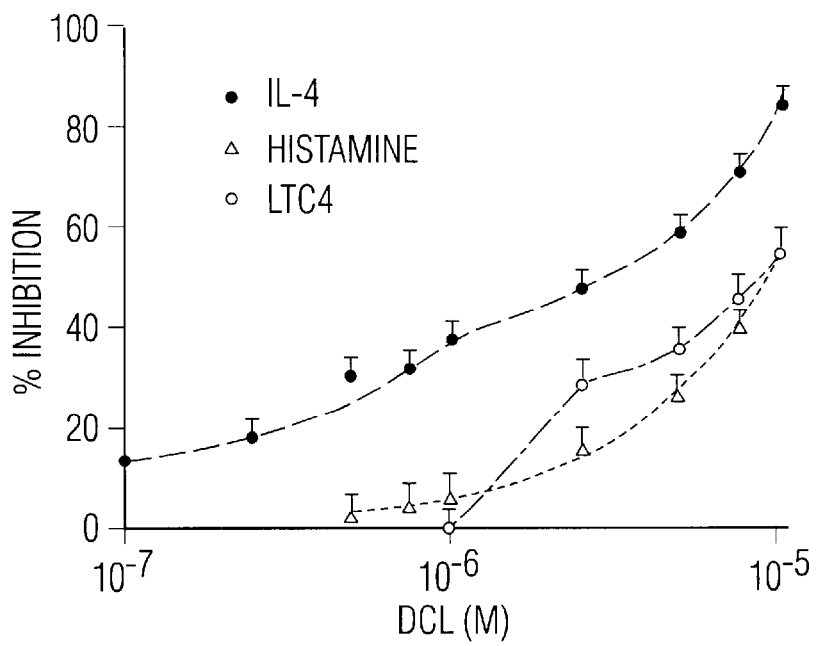
FIGS. 1a and 1b illustrate the effect of desloratadine on histamine, leukotriene $C_4$ ("$LTC_4$") and IL-4 secretion by human basophils.

In accordance with the methods of the present invention, we demonstrated the ability of desloratadine to inhibit the generation of IL-4 and IL-13 from human basophils while concurrently comparing its efficacy in preventing mediator release from these cells using a variety of stimuli. Desloratadine was found to be remarkably (nearly 6–7) times more potent in reducing the secretion of IL-4 and IL-13 from human basophils induced by anti-IgE than it was at inhibiting the mediators, histamine and $LTC_4$, released in the same culture supernatants. The cytokines, IL-4 and IL-13, were equally inhibited by desloratadine following activation with ionomycin despite the lack of an effect on the histamine release induced with ionomycin. Desloratadine had a lesser effect at inhibiting the IL-13 secreted in response to IL-3 and PMA, suggesting that the antihistamine differentially targets individual pathways of cytokine generation. Finally, there was no evidence that desloratadine was cytotoxic, i.e., that it mediated its inhibitory effects by causing decreased cell viability. In accordance with the present invention, IL-4 mRNA accumulation was also remarkably inhibited, by as much as 80%, following pretreatment with desloratadine, suggesting that desloratadine targets signals regulating cytokine gene transcription in addition to those controlling mediator release.

The phrase "an allergic and/or inflammatory condition" means those allergic and inflammatory conditions and symptoms found on the skin,eyes, intestinal tract and/or in the upper and lower airway passages from the nose to the lungs. Typical allergic and/or inflammatory conditions of the skin or upper and lower airway passages include seasonal and perennial allergic rhinitis, non-allergic rhinitis, asthma including allergic and non-allergic asthma, sinusitis, colds, dermatitis, especially allergic and atopic dermatitis, and urticaria and symptomatic dermographism. Typical allergic and/or inflammatory conditions of the eyes include, but are not limited to, allergic conjunctivitis. Typical allergic and/or inflammatory conditions of the intestinal tract, but are not limited to, food allergies.

The term "human" as used herein includes a male or female pediatric subject of less than 12 years of age to less than 18 years of age, a male or female pediatric subject of greater than 12 years of age to less than 18 years, and male and female adults of 18 years of age and older.

The term "pro-inflammatory cytokines" as used herein means those cytokines associated with allergic and inflammatory reactions of the skin, eyes, intestinal tract, and airway passages of humans exposed to allergens. Typically suitable pro-inflammatory cytokines include IL-3, IL-4, IL-5, IL-6, IL-8, IL-9 and IL-13.

The amount of desloratadine effective for treating or preventing allergic and inflammatory conditions of the skin or airway passages will vary with the age, sex, body weight and severity of the allergic and inflammatory condition of the patient. Typically, the amount of desloratadine effective for treating or preventing such allergic and inflammatory conditions in an adult human of age older than 12 is in the range of about 2.5 mg/day to about 45 mg/day, preferably about 2.5 mg/day to about 20 mg/day, or about 5.0 mg/day to about 15 mg/day, or about 5.0 mg/day to about 10 mg/day, more preferably about 5.0 mg/day to about 7.5 mg/day, and most preferably about 5.0 mg/day in single or divided doses, e.g., 2×2.5 mg/day, or a single dose of 5.0 mg/day.

Desloratadine is a non-sedating long acting histamine antagonist with potent and selective peripheral H1-receptor antagonist activity. In vitro and in vivo animal pharmacology studies have been conducted to assess various pharmacodynamic effects of desloratadine and loratadine. In assessing central nervous system ("CNS") activity in mice, desloratadine was relatively free of producing alterations in behavior, neurologic or autonomic function. The potential for desloratadine to occupy brain H1-receptors was assessed in guinea pigs following IP administration and results suggest poor access to central histamine receptors for desloratadine.

The clinical efficacy and safety of desloratadine has been documented in over 3,200 seasonal allergic rhinitis patients in 4 double-blinded, randomized clinical trials. The results of these clinical studies demonstrated the efficacy of desloratadine in the treatment of adult and adolescent patients with seasonal rhinitis.

Efficacy endpoints in all the studies were Total Symptom Score, Total Nasal Symptom Score, Total Non-nasal Symptom Score, and Health Quality of Life (HQOL) analysis in efficacy trials. Desloratadine (5 mg once daily) significantly reduced the total symptom scores (the sum of individual scores for rhinorrhea, sneezing, congestion/stuffiness, nasal itching, itchy/burning eyes, tearing, ocular redness, and itchy ears/palate). Desloratadine (5 mg) was significantly ($p<0.01$) more effective than placebo in reducing nasal symptoms. An important efficacy endpoint analyzed in the desloratadine studies is the AM NOW total symptom score. This parameter measures the total symptom relief by the patient after 24 hours before taking the next day dose. Statistically significant ($p<0.05$) reductions were maintained for the full 24 hour dosing interval over the entire 5 mg to 20 mg dosage range.

There were no significant differences in the effectiveness of desloratadine (over the entire 5 mg to 20 mg dosage range) across subgroups of patients defined by gender, age, or race. Desloratadine is particularly useful for the treatment and prevention of the nasal (stuffiness/congestion, rhinorrhea, nasal itching, sneezing) and non-nasal (itchy/burning eyes, tearing/watery eyes, redness of the eyes, itching of the ears/palate) symptoms of seasonal allergic rhinitis, including nasal congestion, in patients in need of such treating and/or preventing.

U.S. Pat. No. 4,659,716 discloses methods of making desloratadine, pharmaceutical compositions containing it and methods of using desloratadine and pharmaceutical compositions containing it to treat allergic reaction in mammals.

U.S. Pat. No. 5,595,997 discloses pharmaceutical compositions containing desloratadine and methods of using desloratadine for treating and preventing various disease states, e.g., allergic rhinitis.

U.S. Pat. No. 6,100,274 discloses stable pharmaceutical compositions containing desloratadine suitable for oral administration to treat allergic reactions, e.g., allergic rhinitis.

The pharmaceutical compositions of desloratadine can be adapted for any mode of administration e.g., for oral, parenteral, e.g., subcutaneous ("SC"), intramuscular ("IM"), and intraperitoneal ("IP"), topical or vaginal administration or by inhalation (orally or intranasally). Preferably desloratadine is administered orally.

Such pharmaceutical compositions may be formulated by combining desloratadine or an equivalent amount of a pharmaceutically acceptable salt thereof with a suitable, inert, pharmaceutically acceptable carrier or diluent that may be either solid or liquid. Desloratadine may be converted into the pharmaceutically acceptable acid addition salts by admixing it with an equivalent amount of a pharmaceutically acceptable acid. Typically suitable pharmaceutically acceptable acids include the mineral acids, e.g., $HNO_3$, $H_2SO_4$, $H_3PO_4$, HCl, HBr, organic acids, including, but not limited to, acetic, trifluoroacetic, propionic, lactic, maleic, succinic, tartaric, glucuronic and citric acids as well as alkyl or arylsulfonic acids, such as p-toluenesulfonic acid, 2-naphthalenesulfonic acid, or methanesulfonic acid. The preferred pharmaceutically acceptable salts are trifluoroacetate, tosylate, mesylate, and chloride. Desloratadine is more stable as the free base than as an acid addition salt and the use of the desloratadine free base in pharmaceutical compositions of the present invention is more preferred. See U.S. Pat. No. 6,100,274.

Solid form preparations include powders, tablets, dispersible granules, capsules, cachets and suppositories. The powders and tablets may be comprised of from about 2.5 to about 95 percent active ingredient preferably from about 2.5 to about 20 percent, more preferably from about 2.5 to about 10 percent, or from about 2.5 to about 5 percent and most preferably 5 percent of the active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection. Solid form preparations may be converted into liquid preparations shortly before use for either oral or administration.

Parenteral forms to be injected intravenously, intramuscularly or subcutaneously are usually in the form of sterile solutions and may contain tonicity agents (salts or glucose), and buffers. Opacifiers may be included in oral solutions, suspensions and emulsions. Liquid form preparations may also include solutions for intranasal administration. The liquid form preparations may comprise the same ranges of active ingredient is as used in solid form preparations.

Aerosol preparations suitable for inhalation may include solutions and solids in powder form, which may be in combination with a pharmaceutically acceptable carrier, such as an inert compressed gas, e.g., nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active component, e.g., an effective amount to achieve the desired purpose.

Further, desloratadine may be administered in association with therapeutically effective amounts of steroids, e.g. mometasone furoate, beclomethasone dipropinate or fluticasone propinate, leukotriene inhibitors, e.g., montelukast sodium or zafirlukast, and/or an upper airway passage decongestant including, but not limited to phenylephedrine, pseudoephedrine and phenylpropanolamine or pharmaceutically acceptable salts thereof, in accordance with the dosing levels known to those skilled in the art and as described in the *Physicians' Desk Reference*. The use of the upper airway passage decongestant, pseudoephedrine HCl, is preferred.

EXAMPLES

MATERIALS AND METHODS

Special Reagents

All reagents were purchased unless otherwise noted. Piperazine-N,N'-bis-2-ethanesulfonic acid (PIPES), ionomycin, FMLP, PMA, and fetal bovine serum (FBS) from Sigma Chemical Co. (St. Louis, Mo.); RPMI-1640 and Iscove's modified Dulbecco's medium (IMDM) both with L-glutamine and containing 25 mM N-2-hydroxyethylpiperazine-N'-2-ethanesulfonic acid (HEPES), gentamicin, nonessential amino acids (100×) from Life Technologies, Inc., Grand Island, N.Y.); and Percoll from Pharmacia (Piscataway, N.J.). The desloratadine used in these experiments was supplied by The Schering-Plough Research Institute. A 0.1 M stock solution was made in DMSO, aliquoted, and frozen at −20° C. All pipes-containing buffers were made from stock 10X PIPES (250 mM PIPES, 1.20 M NaCl, and 50 mM KCL, pH 7.3 and stored at 4° C.). Isotonic Percoll, (referred to as 100% Percoll) was made by mixing 9 parts Percoll with 1 part 10X PIPES. PAG contained one-tenth 10X PIPES. 0.003% HAS, and 0.1% D-glucose. PAG-EDTA additionally contained 4 mM EDTA. Percoll solutions used for cell isolation were all made by mixing the appropriate amounts of 100% Percoll with 1X PIPES.

Cell Preparation and Culture

Mixed leukocyte suspensions containing basophils were prepared either using double-Percoll density centrifugation as described (Schroeder, et al., *J. Immunol.,* 1994, Vol. 153: 1808, or by a combination of countercurrent elutriation and Percoll density centrifugation protocols (MacGlashan, et al., *J. Immunol.,* 1994, Vol. 153:3006–3016). The percentages of basophils obtained using these protocols typically ranged between 5–50% and 10–30%, respectively, and were determined by counting Alcian blue positive and negative stained cells on a Spiers-Levy chamber (Gilbert and Ornstein, 1975). For some experiments, the basophils were additionally purified to >99.9% using a negative-selection protocol (Miltenyi Corp., Auburn, Calif.). For all experiments other than those assessing IL-4 mRNA expression, the cells were cultured in 96-well flat-bottom microtiter plates (in duplicate) using IMDM supplemented with 5% heat-inactivated (56° C. for 30 min.) FBS, 1×non-essential amino acids, and 5 $\mu$g/ml gentamicin (C-IMDM). For the analysis of IL-4 mRNA expression, cells in C-IMDM were cultured in autoclaved (RNase-free) 1.5 ml microcentrifuge tubes (see below), since this allowed for a more precise way to quantitatively isolate mRNA without the need for transferring cells from culture wells before extraction. For each condition, leukocyte suspensions containing approximately 100,000–500,000 basophils in 100 $\mu$l of C-IMDM were prewarmed to 37° C. before adding 100 $\mu$l of desloratadine concentrations in C-IMDM also prewarmed to 37° C. After 15 minutes preincubation, the cells were then activated by adding 50 $\mu$l of 5×(5 times the final concentration) of stimulus. It is important to note here that the concentrations of stimuli used were optimal for IL-4 generation rather than mediator release. This is particularly true for anti-IgE antibody, which has been shown to induce IL-4 at concentrations 10-fold less than those causing optimal histamine release (Schroeder, et al., ibid). For harvesting, cultures were centrifuged and cell-free supernatants collected for mediator release and cytokine analysis, as described (Schroeder, et al., ibid). Histamine, $LTC_4$, and IL-4 were all measured in aliquots of culture supernatant taken at 4 hours. For histamine, this meant taking 20–50 $\mu$l of supernatant and diluting it in 1 ml of PAG buffer containing 1.6% $HClO_4$. After an overnight precipitation at 4° C., the samples were assayed by automated fluorimetry (Siraganian,R. P., *Anal. Biochem.* 1974, Vol.57:383–394). $LTC_4$ was measured by an in-house RIA (MacGlashan, et al., *J. Immunol.* 1986, Vol.136:2231–2239). IL-4 protein was measured by a commercial ELISA (Biosource International). Culture supernatants were harvested after 20 hours incubation for all experiments investigating the effects of desloratadine on IL-13 secretion. In some instances, IL-4 was also measured at this time point, particularly when ionomycin was used, since the kinetics for the secretion of this cytokine extend beyond 4 hours with this stimulus (Schroeder, et al., *J. Leuk. Biol.,* 1998, Vol. 63:692–698). IL-13 protein measurements were also made using a commercial ELISA (Immunotech).

RNA Isolation and Semi-Quantitative Analysis of IL-4 mRNA Expression

Cultures for the analysis of IL-4 mRNA were performed in 1.5 ml polypropylene microcentrifuge tubes, as described above. Cells were pretreated with desloratadine (10 $\mu$M) for 15 minutes prior to activating with anti-IgE antibody (10–20 ng/ml). Total RNA was isolated using the RNAzol protocol (Tel-test Inc., Friendswood, Tex.) after 2 hours incubation, which is the time that IL-4 message expression peaks using IgE-dependent activation (Schroeder, et al., *J. Immunol.* 1997, Vol.158:5448–5454). Following isopropanol precipitation, the RNA was washed with 70% ethanol and dried under vacuum. Subsequently, the RNA was resuspended in 25 $\mu$l of diethipyrocarbonate (DEPC)-treated water and stored at −80° C. Reverse Transcription (RT) and polymerase chain reaction (PCR) were performed with serial dilutions of RNA as previously detailed (MacGlashan, et al., *J. Immunol,* 1994; Vol. 152:3006–3016; Schroeder, at al., *J. Immunol.,* 1997, Vol. 158: 5448–5454) using the GeneAmp RNA PCR kit (Perkin-Elmer Cetus, Norwalk, Conn.). PCR products were visualized in 3% agrose gels using ethidium bromide staining. As noted elsewhere, two distinct bands for IL-4 were observed. A dominant band was seen with a size of approximately 460 bp. The source of the smaller, fainter band is uncertain, but is thought to be an alternatively spliced form of IL-4 (Atamas, et al., *J. Immunol,* 1996, Vol.156:435–441). The two bands are routinely observed using either pure or enriched suspensions of basophils.

Figure 1B:
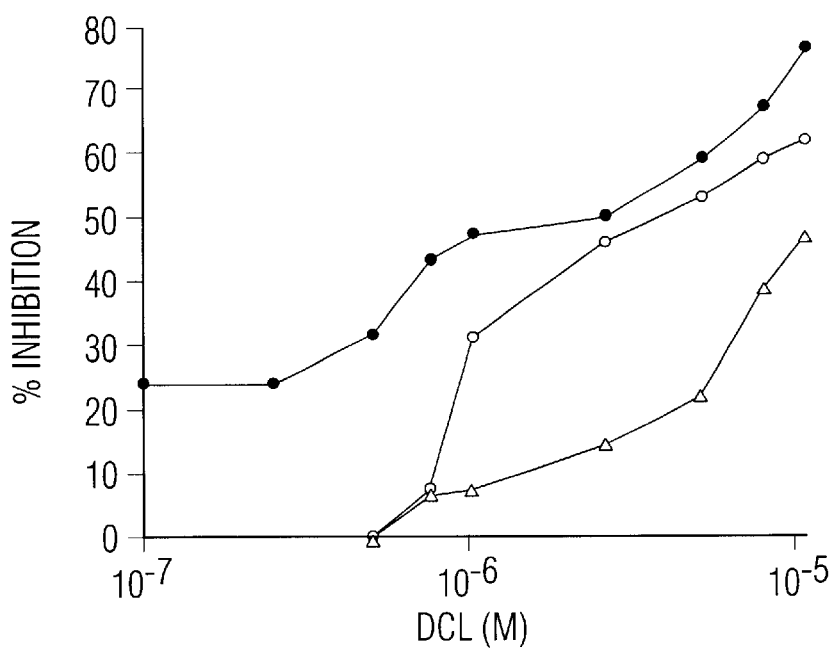

FIGS. 1a and 1b graphically illustrate the effect of desloratadine on histamine, $LTC_4$, and IL-4 secretion by human basophils. For FIG. 1a, mixed leukocyte suspensions containing 3–55% basophils were prepared from whole blood using Percoll density centrifugation. Cells were pretreated 15 min. with the indicated concentrations of desloratadine before activating with anti-IgE antibody (10–20 ng/ml). All three products were measured using the same culture supernatants harvested after 4 hours incubation. Values are the mean±SEM (n=5). Control release for each product: Histamine: 40±6% of total, IL-4: 403±207 pg/$10^6$ basophils, and $LTC_4$: 860±127 pg/$10^6$ basophils. FIG. 1b shows the effect of desloratadine on histamine, $LTC_4$, and IL-4 secretion from human basophils, 99% purity. Control release for histamine, $LTC_4$, and IL-4 were 60% of total, 903 pg/$10^6$ basophils, and 854 pg/$10^6$ basophils, respectively.

Figure 2:
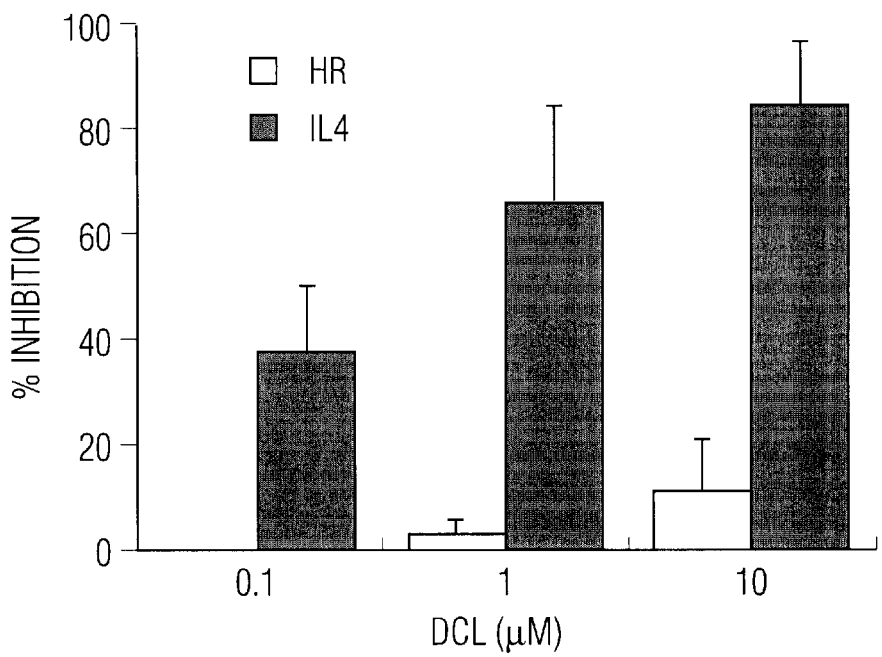
FIG. 2 graphically illustrates the effect of desloratadine on histamine release and IL-4 secretion in response to activation by ionomycin.

FIG. 2 illustrates the effect of desloratadine on histamine release (HR) and IL-4 secretion in response to ionomycin. Basophil suspensions of 42, 99, and 98% purity were pretreated 15 min. with 0.1, 1.0, and 10 $\mu$M desloratadine. Cells were then activated with ionomycin (500 ng/ml) for 4 hours. Culture supernatants were harvested and assayed for histamine and IL-4 protein. Values represent the mean±SEM, n=3. Control levels of IL-4 were 3398, 253, and 348 pg/$10^6$ basophils. Percent histamine release in the same cultures was 91, 25, and 10%, respectively.

Figure 3:
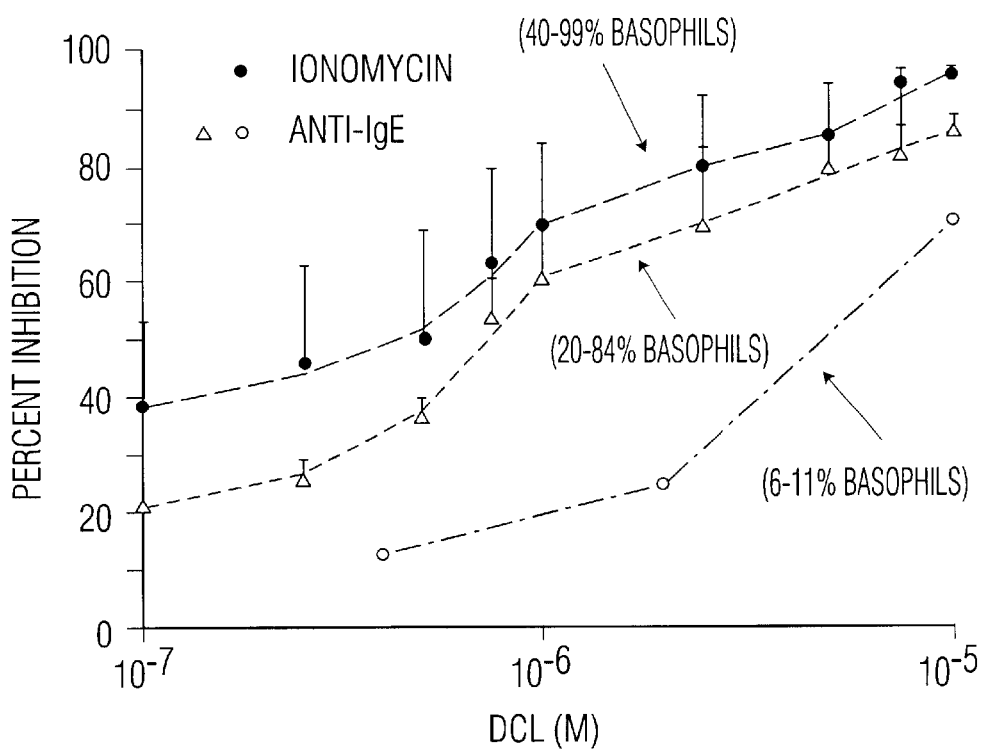
FIG. 3 graphically illustrates the effect of desloratadine on IL-13 secretion by human basophils activated by anti-IgE and ionomycin.

FIG. 3 illustrates the effect of desloratadine on IL-13 secretion by human basophils activated by anti-IgE or ionomycin. Basophil suspensions ranging in purity between 6–99% were pretreated 15 min. with the indicated concentrations of desloratadine. Cells were activated with either anti-IgE (10–20 ng/ml) or ionomycin (500 ng/ml). Culture supernatants were harvested after 18 hours incubation and assayed for IL-13 protein by ELISA. Values with error bars represent the mean±SEM, n=3. IL-13 protein in control cultures averaged 169±35 and 334±144 pg/$10^6$ basophils for anti-IgE and ionomycin, respectively. Values indicated by the open circles are the mean for two experiments (control levels of IL-13 were 260 and 230 pg/$10^6$ basophils).

Figure 4:
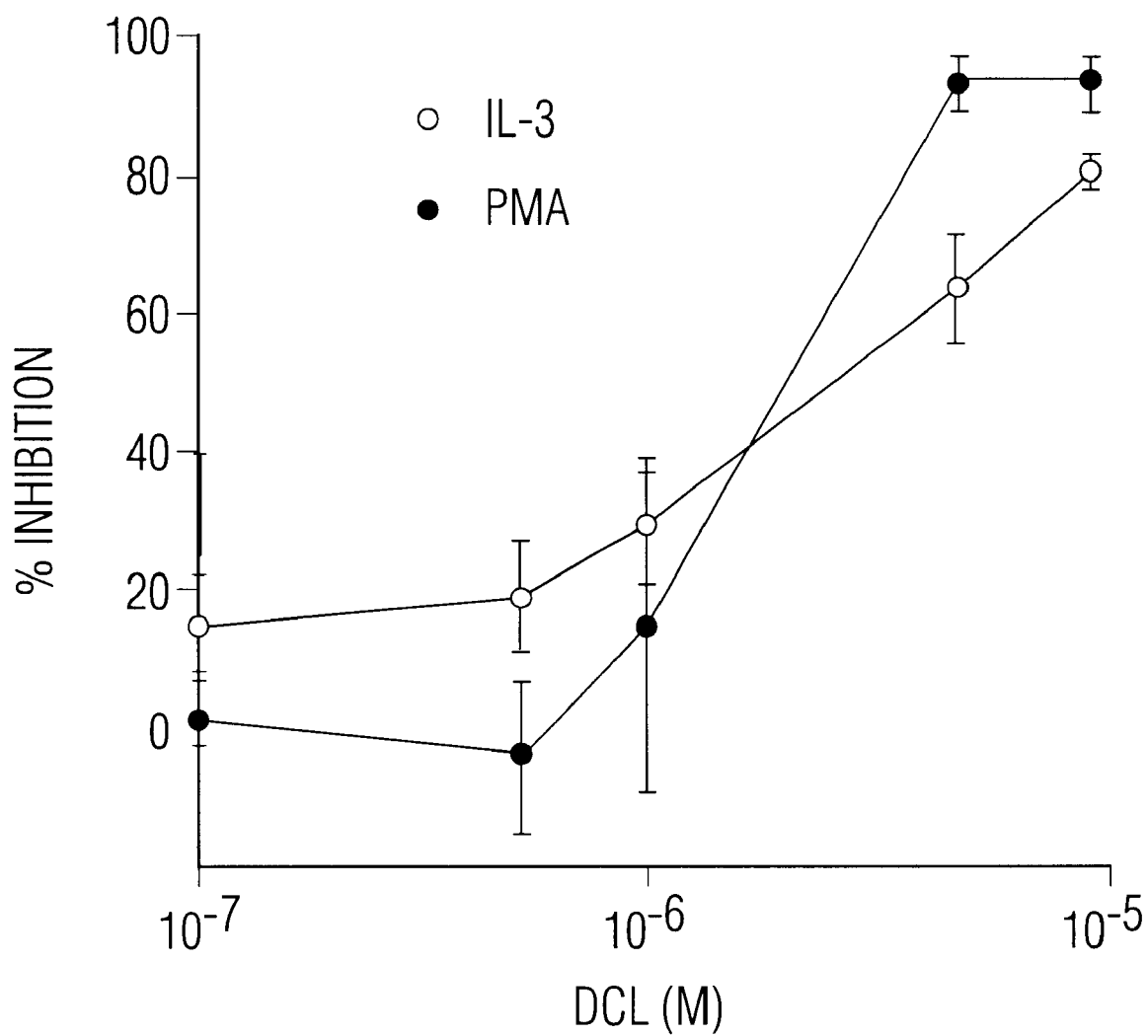
FIG. 4 graphically illustrates that desloratadine inhibits IL-13 secretion from basophils activated with IL-3 and PMA.
Figure 5A:
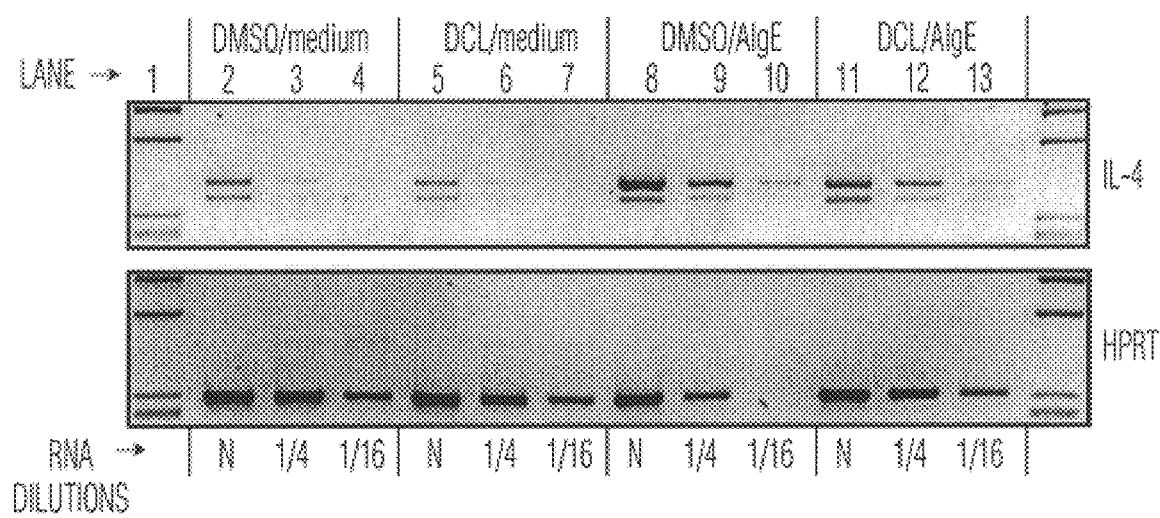
FIGS. 5a, 5b, 5c and 5d graphically illustrate the inhibition of IL-4 mRNA expression in basophils pretreated with desloratadine.
Figure 5B:
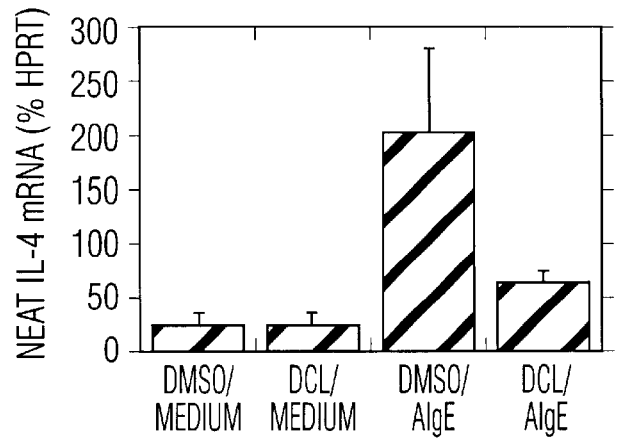
Figure 5C:
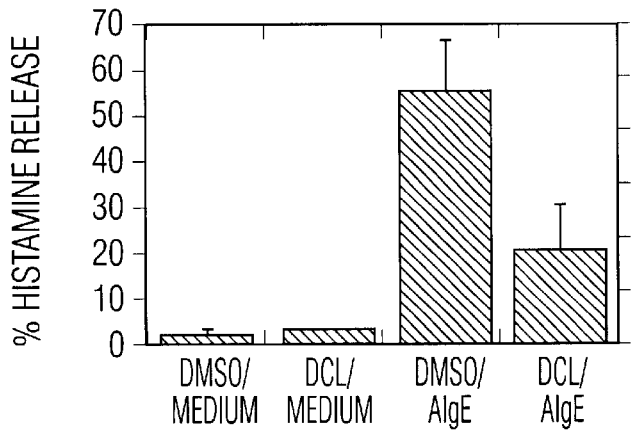
Figure 5D:
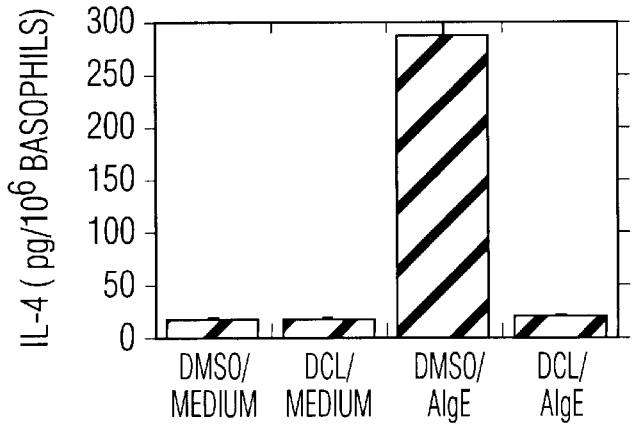

FIG. 4 graphically illustrates that desloratadine inhibits IL-13 secretion from basophils activated with IL-3 and PMA. Basophils (up to 94% purity) were prepared from whole blood using double Percoll density centrifugation and negative selection protocols. Cells were pretreated with the indicated concentrations of desloratadine before adding IL-3 (100 ng/ml) or PMA (2 ng/ml). Culture supernatants were harvested after 18 hours incubation and assayed for IL-13 protein by ELISA. Values represent the mean±SEM, n=3–4. The amount of IL-13 secretion in the absence of desloratadine averaged 570±142 pg/$10^6$ basophils for IL-3 activation and 216±120 pg/$10^6$ basophils for PMA induction.

FIGS. 5a–d graphically illustrate the inhibition of IL-4 mRNA expression in basophils pretreated with desloratadine. Cells were incubated 15 min. with desloratadine (10 $\mu$M) or DMSO (1:10,000) before receiving anti-IgE (10 ng/ml) or medium alone. Total RNA was isolated after 2 h and used for dilutional RT-PCR analysis to compare message expression for IL-4 and the housekeeping gene, hypoxanthine phosphoribosyl transferase (HPRT) (panel a). Densitometric analysis is shown for undiluted RNA expression (panel b). The histamine and IL-4 secretion in the supernatants after 2b are shown for comparison (panels c and d, respectively). Values represent the mean±SEM, n=3.

DISCUSSION

In the first series of experiments (See FIGS. 1a & 1b), we demonstrated the ability of desloratadine to block IL-4 secretion from basophils triggered by anti-IgE, and compared this inhibition to that seen for histamine and $LTC_4$ release in the same 4 h culture supernatants. As shown in FIG. 1a, desloratadine dose-dependently inhibited the release of histamine and $LTC_4$ at concentrations between 1 $\mu$M ($10^{-6}$ M) and 10 $\mu$M ($10^{-5}$ M). For comparison, desloratadine was strikingly more potent against IL-4 secretion than for preformed mediator release. Cells pretreated with 1 $\mu$M to 10 $\mu$M desloratadine secreted 40% to 80% less IL-4 than cells not exposed to drug. Nearly a seven-fold greater concentration of desloratadine was necessary to cause a comparable inhibition in the release of histamine and $LTC_4$ by these cells. The inhibition of IL-4, unlike that seen for histamine, appeared to plateau in the micromolar range of desloratadine and then reached progressively higher values at concentrations between 1 $\mu$M and 10 $\mu$M desloratadine. As shown in FIG. 1b, this effect was also evident using basophils purified to greater than 99%, indicating that desloratadine was directly affecting basophils for the inhibition of IL-4. Desloratadine also inhibited histamine from pure basophils much as it did for impure suspensions.

We tested whether desloratadine affected IL-4, histamine, and $LTC_4$ release from basophils activated by other stimuli. FIG. 2 shows that the secretion of histamine induced by the calcium ionophore, ionomycin, was unaffected by desloratadine at concentrations of 0.1, 1.0, and 10 $\mu$M. However, the high levels of IL-4 that were secreted in response to ionomycin stimulation were remarkably inhibited by the same concentrations of desloratadine (i.e. 0.1, 1.0 and 10 $\mu$M). The histamine and $LTC_4$ made in response to FMLP stimulation was also not inhibited by desloratadine (data not shown).

Redrup, et al., *J.Immunol.*, 1998, Vol.160:1957–1964 reported that (1) multiple stimuli induce pharmacologically distinct pathways for the generation of IL-13 in human basophils and that (2) both anti-IgE and ionomycin induced IL-13 secretion that was sensitive to the immunosuppressive drug, FK-506, suggesting that these stimuli utilize a calcineurin-dependent pathway to generate this cytokine. In the Redrup, et al study, the IL-13 made in response to IL-3 or PMA activation was unaffected by FK-506, and only protein generated in response to the phorbol ester was inhibited by PKC inhibitors. Therefore, we addressed whether the IL-13 induced by these stimuli is also differentially affected with desloratadine pretreatment. FIG. 3 shows that IL-13 generated in response to either anti-IgE or ionomycin. In fact, there was remarkable similarity in the shape of the concentration-response curve of desloratadine for inhibition of IL-13 induced by either stimulus. These curves in FIG. 3 were nearly identical to that seen for the inhibition of IL-4 by desloratadine as shown in FIGS. 1 and 2. In particular, an initial plateau was seen at 1 $\mu$M at the level of 50–70% inhibition. Dose-dependent inhibition of IL-13 continued as desloratadine concentrations were increased up to 10 $\mu$M. Interestingly, the response to desloratadine pretreatment was considerably different in two experiments using impure (6–11%) basophil suspensions. With these cell preparations, desloratadine was considerably less effective in preventing the IL-13 secreted in response to anti-IgE, requiring nearly 10-fold greater concentrations to produce the same $IC_{50}$ seen using more pure basophil suspensions. FIG. 4 shows that desloratadine also inhibited the IL-13 made in response to IL-3 or PMA, albeit to a lesser extent and with inhibition curves that appeared more log-linear. In fact, the drug inhibited IL-3-mediated IL-13 production with an $IC_{50}$ of approximately 2 $\mu$M, which was nearly 5-fold that necessary to inhibit the IL-13 secreted with anti-IgE or ionomycin activation. Desloratadine inhibited the IL-13 induced by PMA in similar fashion, with inhibition seen between 1 $\mu$M and 10 $\mu$M concentrations of drug.

Unlike histamine and $LTC_4$, both of which are released from basophils within minutes after activation, IL-4 protein is first detected after 1–2 hours and IL-13 some 48 hours after activation. Therefore, it seemed possible that the kinetics of mediator release vs. cytokine production might account for the differences in their sensitivity to desloratadine, particularly if cell lysis was a factor. However, we saw no evidence that 10 $\mu$M desloratadine, even when combined with stimulus for 18 hours, was cytotoxic, i.e., caused cell death as assessed by trypan blue exclusion in pure basophil cultures (data not shown). Cells did stain with trypan blue when cultured with 100 $\mu$M desloratadine alone. Furthermore, histamine was detected in these cultures, indicating that this concentration of desloratadine caused cell lysis.

Finally, to investigate the possibility that desloratadine inhibits cytokine secretion from basophils by affecting the accumulation of mRNA, we examined the effect of desloratadine (10 $\mu$M) pretreatment on the expression of IL-4 message. For these experiments, we used a dilutional RT-PCR protocol to provide a semi-quantitative analysis. Panel a of FIG. 5 clearly shows that IL-4 mRNA expression was induced in cells activated with anti-IgE (lanes 8–10) relative to cells not receiving stimulus (lanes 2–4). Pretreatment with desloratadine resulted in a substantial decrease of the induced cytokine message (lanes 11–13), while having no effect on the expression of the housekeeping gene, HPRT. Panel b of FIG. 5 shows the average densitometric analysis of three experiments, indicating that desloratadine pretreatment caused approximately an 80% reduction in the IL-4 message accumulated with anti-IgE activation. For comparison, desloratadine (10 $\mu$M) also inhibited the histamine and IL-4 protein secreted into the supernatants of these cultures, as shown in panels c and d, respectively, of FIG. 5.

Our findings support the concept that the mechanisms underlying the efficacy of H1-antagonists in the treatment of allergic rhinitis extend beyond their ability to prevent histamine from binding to its H1 receptor by showing that desloratadine possesses inhibitory activity against the generation of IL-4 and IL-13 from human basophils. Others have shown that desloratadine prevents IgE-mediated histamine release and $LTC_4$ generation by human basophils and our results confirm these findings (See Kleine-Tebbe, et al., 1994; and Genovese, et al., *Clin. Exp. Allergy*, 1996, Vol. 27:559–567). However, in accordance with this invention, we have shown that desloratadine is remarkably (6 to 7-fold) more effective at inhibiting IL-4 and IL-13 induced by anti-IgE than it is at blocking histamine and $LTC_4$ release in these cultures. Interestingly, in accordance with this invention, desloratadine inhibited IL-4 and IL-13 with a dose response curve that plateaued at 1 and 10 $\mu$M concentrations. (See FIG 1b.) This effect was not seen for mediator release and occurred only for cytokine (IL-4 and IL-13) produced in response to anti-IgE or ionomycin. While the nature of this inhibition is presently unknown, we predict that desloratadine targets at least two signals along with common pathway triggered by both stimuli. Thus, at concentrations below 1 $\mu$M desloratadine, the inhibition may result from disruption of a signal involved only in cytokine generation, while at concentrations above 1 $\mu$M, a second signal may also be affected, resulting in inhibition of preformed mediator release for most stimuli.

We found desloratadine to be less effective at preventing mediator release induced by IgE-independent stimuli, such as ionomycin, fmip, and phorbol ester. In fact, we found no evidence that the histamine and/or $LTC_4$ released with these stimuli were inhibited by any of the desloratadine concentrations tested (data not shown). In contrast, desloratadine was quite effective in blocking the production of IL-4 induced by ionomycin and the IL-13 generated in response to either ionomycin, PMA, or IL-3. As noted above, desloratadine equally inhibited the IL-4 and IL-13 induced by ionomycin or anti-IgE with inhibition curves that plateaued at 1 and 10 $\mu$M concentrations of drug. However, the same pattern and potency of inhibition was not observed for the inhibition of IL-13 induced by IL-3 or PMA. With regard to cytokine production, both anti-IgE and ionophore induced IL-4 and IL-13 that are inhibited by the immunosuppressive drug, FK506, suggesting that these stimuli utilize a calcium-dependent calcineurin pathway for the generation of these cytokines. However, desloratadine does not block the IL-13 made in response to IL-3 or PMA, both of which are thought to activate separate pathways. Thus, desloratadine may inhibit IgE-dependent cytokine secretion and mediator release by simply preventing changes in cytosolic calcium. This effect, however, does not fully explain why desloratadine inhibited cytokine induced by ionomycin while having no effect on mediator release. Since IgE-crosslinking and $Ca^{2+}$ ionophores appear to activate calcineurin in basophils, it is possible that desloratadine targets a factor within pathway initiated by this phosphatase.

By using pure basophil suspensions we were able to conclude for the first time whether desloratadine mediates its inhibitory effect on basophil mediator release and cytokine production directly. We could detect no evidence, as assessed by trypan blue exclusion, that the decreased IL-4 and IL-13 secreted was accompanied by increased cell death during the 4-20 hour incubations. This was true even with 10 $\mu$M desloratadine which caused nearly complete(>95%) inhibition of cytokine secretion. Cell lysis was observed at a concentration of 100 $\mu$M.

In accordance with the methods of the present invention, we have demonstrated that desloratadine inhibits the accumulation of IL-4 mRNA, supporting the concept that desloratadine can negatively regulate factors important for cytokine gene transcription. Interestingly, desloratadine pretreatment resulted in nearly 80% inhibition of the IgE-mediated increase of IL-4 mRNA. However, the secretion of protein for this cytokine (IL-4) in the same cultures was below detection, and was thus inhibited >95%. Once again this may imply that desloratadine targets multiple pathways in the generation of cytokines, affecting more than just signals important for gene transcription. In fact, it remains possible that transcription is not at all affected but that IL-4 and IL-13 mRNA is made unstable in some way and that this accounts for the inhibitory action of desloratadine. If so, the instability must be specific for cytokine mRNA, since our results demonstrated that housekeeping gene (HPRT) expression is unaffected by desloratadine.

We expect that inhibitory effects of desloratadine on cytokine generation and mediator release seen in these in vitro studies should translate into the clinical efficacy of desloratadine against allergic and inflammatory conditions of the skin, e.g., atopic dermatitis and urticaria, and in the eyes, e.g., allergic conjunctivitis, and in the intestinal tract, e.g., food allergies, and in the upper and lower airway passage, e.g., allergic rhinitis, especially seasonal allergic rhinitis. Given the fact IL-4 and IL-13 help regulate the synthesis of IgE, activate endothelium for VCAM-1-mediated eosinophil transmigration, and that IL-4 promotes the development of the T-helper 2 phenotype, we expect that desloratadine will mediate anti-allergic activity, not only by inhibiting mediator release, but also by blocking the generation of pro-inflammatory cytokines IL-3, IL-4, IL-5, IL-6, IL-8, IL-9 and IL-13.

CLINICAL STUDIES

The following clinical studies are designed to show that desloratadine provides combined antihistaminic and anti-allergic inflammatory effects to control both early and late phase allergic reactions and clinical symptoms on human subjects exposed to allergens or exhibiting the signs and symptoms of allergic and/or inflammatory diseases of the skin, eyes intestinal tract, and airway passages.

STUDY NO. 1

Objective

To demonstrate that nasal allergen provocation of atopic human subjects induces systemic allergic/immunologic effects, such as, increased cytokine production by basophils and lymphocytes, and that this will be manifested in vitro (increased cytokine release) and in vivo (increase in late-phase reaction in allergen-induced skin reaction).

Study Design

This will be an open-label, non-therapeutic, pilot study, involving 6 to 10 asymptomatic atopic subjects with documented histories of seasonal allergic rhinitis (and possibly allergic asthma) who will be challenged nasally with allergen on 3 consecutive days.

Blood specimens will be collected 3 days before beginning the nasal challenges, daily prior to each challenge, and one week after the first challenge. Basophils and lymphocytes will be isolated using standard Percoll gradient techniques and their RNA will be extracted and tested using a real time PCR assay with primers for IL-3, IL-4, IL-5, IL-6, IL-9 IL-13, IL-5 and RANTES.

The mRNA for these cellular products will be quantitated by comparison to the PCR product of a housekeeping gene (GAPDH). Leukocyte differential, and total eosinophil and basophil counts will be used to assess the potential effect of changes in cell numbers on allergen-induced changes in cytokine/chemokine mRNA.

Dose-titrated allergen-induced skin wheal reaction testing will be done at the time of initial blood drawing above (i.e., 3 days prior to the first nasal allergen challenge) and one week after the last nasal allergen challenge.

Nasal symptom severity scores will be monitored during each nasal allergen provocation day. It is expected that induction of cytokine transcription will correlate to worsening nasal symptomatology.

Primary Endpoint:

Based on in vitro data, the expected primary outcome should be allergen-induced increases in inflammatory cells and up-regulation of IL-4 and IL-13 transcription in the skin biopsy tissue.

Secondary Endpoints:

Changes from baseline in peripheral leukocytes, including eosinophils, basophils and lymphocytes.

Changes from baseline in cytokine production by leukocytes.

Change from baseline in the size of the allergen-induced skin wheal late phase reaction.

Correlation of the above changes with clinical symptomatology.

STUDY NO. 2

Objective

Identification of the biochemical and clinical effects of the anti-allergic and anti-inflammatory properties of desloratadine.

A study of the effects of desloratadine on the induction of peripheral blood leukocyte cytokines by nasal allergen provocation in atopic human subjects: a preliminary clinical study to demonstrate that desloratadine provides combined antihistaminic and anti-allergic effects to control early and late phase allergic reaction and clinical symptoms in human subjects exposed to nasal allergen provocation. The number of subjects for Study No. 2 will be determined based on the findings in the pilot in vitro and clinical study.

Hypotheses

There is evidence that nasal allergen provocation of atopic individuals induces systemic effects, e.g., peripheral blood eosinophil counts are increased between 6 to 24 hours following this procedure and consistent increases in lower airway responsiveness, in patients with allergic rhinitis and asthma, have followed nasal allergen provocation. It is possible that the systemic effects of allergic rhinitis are mediated through increased proliferation of peripheral leukocytes and increased cytokine production by these cells. The underlying rationale for these hypotheses is that these phenomena are dependent on the state of activation in immune cells, including basophils and lymphocytes.

Study Design

The clinical efficacy will involve the same essential nasal allergen challenge design and blood specimen collections and allergen-induced skin wheal testing as in Study No. (See below.) Study No. 2, however, will be a double-blind, placebo-controlled, cross-over design during which desloratadine (5 mg once daily) and placebo will be taken daily for 5–7 days prior to the first blood drawing and throughout the remainder of the testing period: the repeat allergen-induced skin wheal test will occur one week after the last nasal allergen challenge. The number of subjects for this study will be determined by power analysis dependent on the results of the preliminary study. A two-week washout period will intervene between the two treatment periods.

| Flow Chart (Study Days) | | | | |
|---|---|---|---|---|
| −3 (baseline) | 0 | 1 | 2 | 9 |
| blood drawn | nasal allergen challenge** | nasal allergen challenge** | nasal allergen challenge** | skin wheal test |
| skin wheal test | blood draw* dosing | blood draw* dosing | blood draw* → dosing | dosing |

*for leukocyte differential, total eosinophil and basophil counts for isolation of basophils and lymphocytes and extraction of their RNA for PCR assay (IL-4, IL-3, IL-13, IL-5, IL-6 and RANTES)
**clinical symptoms and severity scoring Clinical Efficacy Endpoints Comparisons of results will be made between treatment groups and within treatment groups for:

Changes from baseline in peripheral leukocytes, including eosinophils, basophils and lymphocytes.

Changes from baseline in cytokine production.

Changes from baseline in the size of the allergen-induced skin wheal late phase reaction.

Correlation of the above changes with clinical symptomatology.

Desloratadine is expected to provide combined antihistamine and anti-allergic inflammatory effects to control both early and late phase allergic reactions and clinical symptoms in humans.

We claim:

1. A method for treating ocular allergic and/or ocular inflammatory symptoms while concurrently inhibiting secretion of IL-4 and IL-13 in a patient exhibiting or at risk to exhibit said symptoms, comprising administering to said patient an effective amount of desloratadine.

2. A method for treating intestinal allergic and/or intestinal inflammatory symptoms while concurrently inhibiting secretion of IL-4 and IL-13 in a patient exhibiting or at risk to exhibit said symptoms, comprising administering to said patient an effective amount of desloratadine.

3. A method for inhibiting generation of IL-4 and IL-13 from human basophils in a patient exhibiting ocular allergic and/or ocular inflammatory symptoms, comprising administering to said patient an amount of desloratadine effective to inhibit the generation of IL-4 and IL-13 and to concurrently treat said symptoms.

4. A method of inhibiting generation of IL-4 and IL-13 from human basophils in a patient exhibiting intestinal allergic and/or intestinal inflammatory symptoms, comprising administering to said patient an amount of desloratadine effective to inhibit the generation of IL-4 and IL-13 and to concurrently treat said symptoms.

* * * * *